US011045475B2

(12) United States Patent
Zuo et al.

(10) Patent No.: US 11,045,475 B2
(45) Date of Patent: Jun. 29, 2021

(54) APPLICATION OF METHYL 4-[9-(6-AMINO-PURYL)]- 2(S)-HYDROXYBUTYRATE IN PREPARATION OF MEDICAMENT FOR TREATING PSORIASIS AND VITILIGO

(71) Applicants: SHANGHAI INSTITUTE OF MATERIA MEDICA, CHINESE ACADEMY OF SCIENCES, Shanghai (CN); NINGBO ZIYUAN PHARMACEUTICALS INC., Zhejiang (CN)

(72) Inventors: Jianping Zuo, Shanghai (CN); Wei Tang, Shanghai (CN); Zemin Lin, Shanghai (CN); Chongsheng Yuan, San diego, CA (US)

(73) Assignees: SHANGHAI INST. OF MATERIA MEDICA, CHINESE ACADEMY OF SCIENCES, Shanghai (CN); NINGBO ZIYUAN PHARMACEUTICALS INC., Zhejiang (CN)

( * ) Notice: Subject to any disclaimer, the term of this patent is extended or adjusted under 35 U.S.C. 154(b) by 41 days.

(21) Appl. No.: 16/314,024

(22) PCT Filed: Jun. 29, 2017

(86) PCT No.: PCT/CN2017/090684
§ 371 (c)(1),
(2) Date: Dec. 28, 2018

(87) PCT Pub. No.: WO2018/001287
PCT Pub. Date: Jan. 4, 2018

(65) Prior Publication Data
US 2019/0216817 A1 Jul. 18, 2019

(30) Foreign Application Priority Data
Jun. 30, 2016 (CN) .......................... 201610510528.2

(51) Int. Cl.
| | | |
|---|---|---|
| *A01N 37/00* | (2006.01) | |
| *A61K 31/215* | (2006.01) | |
| *A01N 37/12* | (2006.01) | |
| *A01N 37/44* | (2006.01) | |
| *A61K 31/24* | (2006.01) | |
| *A01N 25/00* | (2006.01) | |
| *A61K 31/52* | (2006.01) | |
| *A61P 17/06* | (2006.01) | |
| *A61P 17/00* | (2006.01) | |
| *A61K 9/00* | (2006.01) | |
| *A61K 9/06* | (2006.01) | |
| *A61K 47/42* | (2017.01) | |

(52) U.S. Cl.
CPC .............. *A61K 31/52* (2013.01); *A61P 17/00* (2018.01); *A61P 17/06* (2018.01); *A61K 9/0053* (2013.01); *A61K 9/06* (2013.01); *A61K 47/42* (2013.01)

(58) Field of Classification Search
None
See application file for complete search history.

(56) References Cited

U.S. PATENT DOCUMENTS 8,247,549 B2 * 8/2012 Nan ..................... C07D 473/34
544/277

FOREIGN PATENT DOCUMENTS

CN 101456860 A 6/2009

OTHER PUBLICATIONS

He et al., "The Curative Effect of Reversible S-Adenosine Homocysteine Hydrolase Inhibitor DZ2002 in NZB/WF1 Murine Lupus Models and the Study of Regulatory Mechanism of Dendritic Cells", 8th Congress of the Chinese Society for Immunology, Aug. 31, 2015, pp. 124-125.
Lin et al., "The Study of the Reversible S-Adenosine Homocysteine Hydrolase Inhibitor DZ2002 on the Therapeutic Effects of Mechanism of Psoriasis", Chinese Journal of Pharmacology and Toxicology, Oct. 30, 2016, p. 1089, 30-10.
Fragoulis GE, Siebert S, McInnes IB. Therapeutic Targeting of IL-17 and IL-23 Cytokines in Immune-Mediated Diseases. *Annual review of medicine* 2016; 67: 337-53.
Singh RK, Lee KM, Vujkovic-Cvijin I et al. The role of IL-17 in vitiligo: A review. *Autoimmunity reviews* 2016; 15: 397-404.
Baeten D, Baraliakos X, Braun J et al. Anti-interleukin-17A monoclonal antibody secukinumab in treatment of ankylosing spondylitis: a randomised, double-blind, placebo-controlled trial. *The Lancet* 2013; 382: 1705-13.
Kunwar S, Dahal K, Sharma S. Anti-IL-17 therapy in treatment of rheumatoid arthritis: a systematic literature review and meta-analysis of randomized controlled trials. *Rheumatology international*2016: 36: 1065-75.

(Continued)

*Primary Examiner* — Layla Soroush
(74) *Attorney, Agent, or Firm* — Muncy, Geissler, Olds & Lowe, P.C.

(57) ABSTRACT

Provided in the present invention is a use of methyl 4-[9-(6-aminopuryl)]-2(s)-hydroxybutyrate in the preparation of a medicament for treating psoriasis and vitiligo. More specifically, the present invention uses mice whose psoriasis is induced by an imiquimod cream to observe a changing condition in skin lesions on the psoriasis-like mice, according to a psoriasis skin lesion area of the mice and grading standards for disease severity; the present invention also observes a proportion of lymphocytes in the spleens and cytokines in skin lesion tissues of the mice. A good therapeutic effect may be obtained by treating typical cases of vitiligo with an ointment of methyl 4-[9-(6-aminopuryl)]-2(s)-hydroxybutyrate. Results show that methyl 4-[9-(6-aminopuryl)]-2(s)-hydroxybutyrate used in the present invention has a good therapeutic effect on psoriasis and vitiligo, as well as a favorable prospect in clinical application.

2 Claims, 5 Drawing Sheets

(56) References Cited

OTHER PUBLICATIONS

Havrdova E, Belova A, Goloborodko A et at. Activity of secukinumab, an anti-IL-17A antibody, on brain lesions in RRMS: results from a randomized, proof-of-concept study. *Journal of neurology* 2016: 263: 1287-95.
Lowes MA, Bowcock AM, Krueger JG. Pathogenesis and therapy of psoriasis. *Nature* 2007; 445: 866-73.
Krueger GG, Langley RG, Leonardi C et al. A human interleukin-12/23 monoclonal antibody for the treatment of psoriasis. *The New England journal of medicine* 2007; 356: 580-92.
Papp KA, Langley RG, Lebwohl M et al. Efficacy and safety of ustekinumab, a human interleukin-12/23 monoclonal antibody, in patients with psoriasis: 52-week results from a randomised, double-blind, placebo-controlled trial (PHOENIX 2). *Lancet* (London, England) 2008; 371: 1675-84.
Papp KA, Blauvelt A, Bukhalo M et al. Risankizumab versus Ustekinumab for Moderate-to-Severe Plaque Psoriasis. *The New England journal of medicine* 2017; 376: 1551-60.
Pandya VB, Kumar S, Sachchidanand et al. Combating Autoimmune Diseases With Retinoic Acid Receptor-Related Orphan Receptor-gamma (RORgamma or RORc) Inhibitors: Hits and Misses. *Journal of medicinal chemistry* 2018; 61: 10976-95.
Rodrigues M, Ezzedine K, Hamzavi I et al. Current and emerging treatments for vitiligo. *Journal of the American Academy of Dermatology* 2017; 77: 17-29.
Mery-Bossard L, Bagny K, Chaby G et al. New-onset vitiligo and progression of pre-existing vitiligo during treatment with biological agents in chronic inflammatory diseases. *Journal of the European Academy of Dermatology and Venereology : JEADV* 2017; 31: 181-6.

\* cited by examiner

Normal Control Group    Model Control Group    Oral Treatment Group

Model Control Group    Gelatin Treatment Group

APPLICATION OF METHYL 4-[9-(6-AMINO-PURYL)]-2(S)-HYDROXYBUTY-RATE IN PREPARATION OF MEDICAMENT FOR TREATING PSORIASIS AND VITILIGO

FIELD OF THE INVENTION

The present invention relates to a novel use of methyl 4-[9-(6-aminopuryl)]-2(s)-hydroxybutyrate, more specifically, to a use of methyl 4-[9-(6-aminopuryl)]-2(s)-hydroxybutyrate in preparation of medicaments for treating psoriasis and vitiligo.

BACKGROUND OF THE INVENTION

Psoriasis is a common chronic, relapsing inflammatory dermatosis with typical clinical symptoms of sharply bordered erythema, rash, plaque and scales, of which the pathogenesis is complicated and the etiology is unknown. At present, main treatments of psoriasis are topical ones and steroid hormones are widely applied, such as hydrocortisone butyrate, mometasone furoate, etc. However, the wide application of steroid hormones is restricted due to their side effects of long-term use. The clinical application of tacrolimus, calcipotriol and the like are also restricted for their high price.

Vitiligo is a common, multiple pigmented dermatosis with an incidence of 0.1% to 2%, and it is characterized by white patches caused by localized or generalized depigmentation and turn out to be an acquired skin disorder of localized or generalized depigmentation. Its etiology is complicated and may be related to genetic, autoimmune and neural factors, and the pathogenesis is related to cellular immunity, humoral immunity and relevant cytokines. Numerous experiments have proved that patients with vitiligo are often accompanied by abnormality of immune antibody and complement levels, which suggests that the immune imbalance plays an important role in the pathogenesis of vitiligo.

S-adenosyl-L-homocysteine hydrolase (SAHH) is a ubiquitous enzyme catalyzing the hydrolysis of S-adenosyl-L-homocysteine (AdoHcy) to adenosine and homocysteine (Hcy). Inhibition of SAHH has been known to result in accumulation of intracellular levels of AdoHcy, which inhibits SAHH transmethylation reactions. Based on different inhibition mechanisms of enzymes, SAHH inhibitors are classified into three types. Inhibition of enzyme activity with Type I and II inhibitors of SAHH is irreversible, which would cause toxic side effects due to SAHH widespread presence in cells. The toxic side effects of irreversible inhibitors of SAHH limit the further development of these inhibitors as immunosuppressive drugs. Inhibition of enzyme activity with Type III inhibitors of SAHH is reversible, and the enzyme activity could be restored as the drug activity decreases, thus their toxicity is lower. Methyl 4-[9-(6-aminopuryl)]-2(s)-hydroxybutyrate is a type III inhibitor of SAHH with low cytotoxicity, and shows good therapeutic effect on experimental autoimmune encephalomyelitis (EAE), systemic lupus erythematosus (SLE) and other diseases in animal models. Methyl 4-[9-(6-aminopuryl)]-2(s)-hydroxybutyrate has the following structural formula:

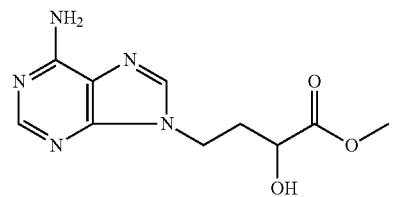 [SMILES: COC(=O)C(O)CCn1cnc2c(N)ncnc21]

At present, there are neither application nor reports on the treatments for psoriasis and vitiligo with methyl 4-[9-(6-aminopuryl)]-2(s)-hydroxybutyrate, and the present invention firstly found the therapeutic effect of methyl 4-[9-(6-aminopuryl)]-2(s)-hydroxybutyrate on psoriasis and vitiligo.

SUMMARY OF THE INVENTION

To solve the aforesaid problems, the present invention provides a use of methyl 4-[9-(6-aminopuryl)]-2(s)-hydroxybutyrate in preparation of medicaments for treating psoriasis and/or vitiligo. Furthermore, the present invention finds that the treatments of methyl 4-[9-(6-aminopuryl)]-2(s)-hydroxybutyrate for psoriasis and vitiligo are more efficient and convenient by topical treatments, with reduced adverse reactions.

The prepared medicaments for treating psoriasis and/or vitiligo may be in any form of ointments, gelatin formulations or oral formulations containing methyl 4-[9-(6-aminopuryl)]-2(s)-hydroxybutyrate.

The present invention firstly discloses the inhibition of the occurrence and development of psoriasis and vitiligo with the methyl 4-[9-(6-aminopuryl)]-2(s)-hydroxybutyrate in the mouse models.

BRIEF DESCRIPTION OF THE DRAWINGS

FIGS. 1A, 1B, 1C, and 1D are the histograms of the scores of erythema, scales, skin thickening, and total scores, successively.

FIG. 2C is for CD3$^+$ CD4$^+$ T cells, and FIGS. 2D and 2E show the ratio of CD3$^+$CD4$^+$ T cells in all spleen lymphocytes.

Figure 3:
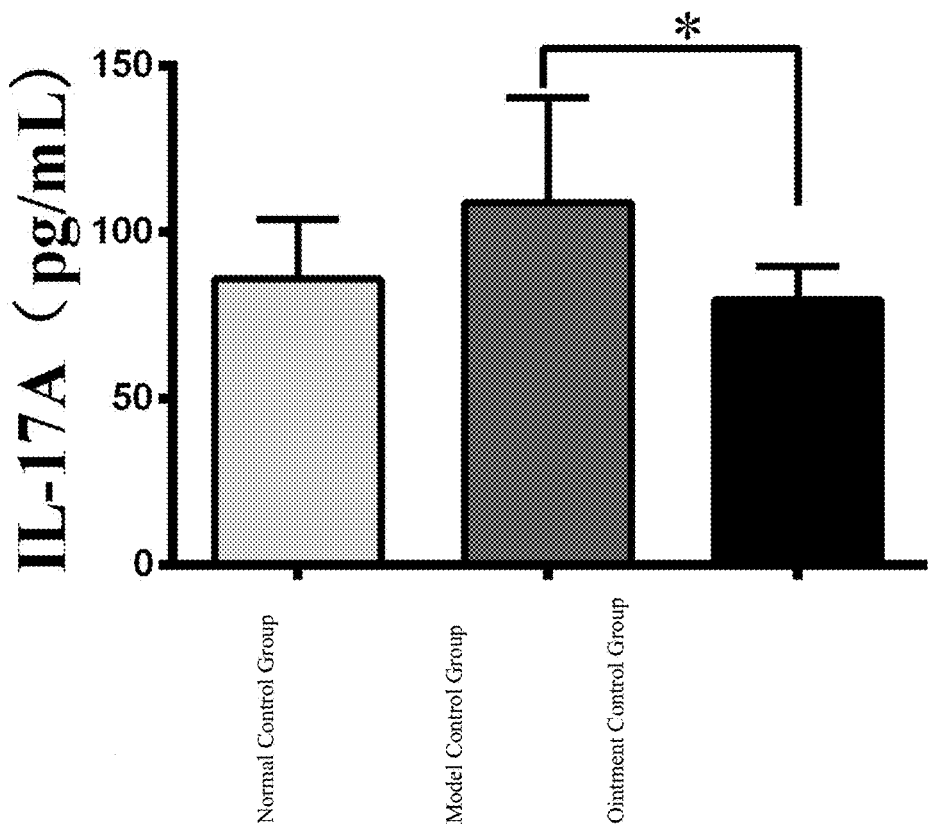
FIG. 3 illustrates the inhibition of IL-17 level in psoriatic lesions induced by imiquimod with methyl 4-[9-(6-aminopuryl)]-2(s)-hydroxybutyrate in mice. Skin of the lesions is taken on Day 7 of imiquimod-induced psoriasis modeling, and its IL-17 content is detected by ELISA. *P<0.05, n≥5.

The groups in FIG. 3 are the normal control group, model control group and ointment treatment group.

Figure 4:
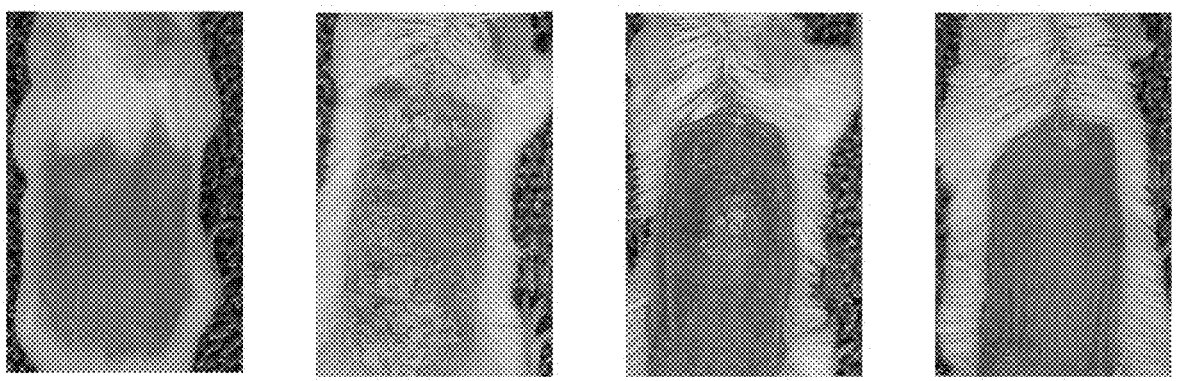

FIG. 4 illustrates the remission of skin lesions with a methyl 4-[9-(6-aminopuryl)]-2(s)-hydroxybutyrate ointment in mice with psoriasis. It is a typical representative diagram, showing skin lesions of the normal control group, model control group, calcipotriol ointment control group and treatment group with the methyl 4-[9-(6-aminopuryl)]-2(s)-hydroxybutyrate ointment in mice with psoriasis induced by imiquimod on Day 7.

Figure 5:
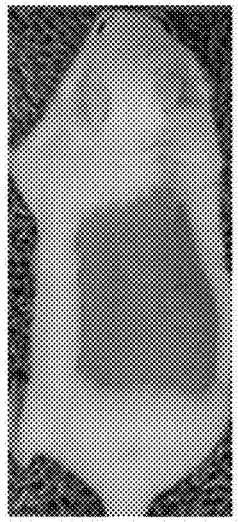
Figure 5:
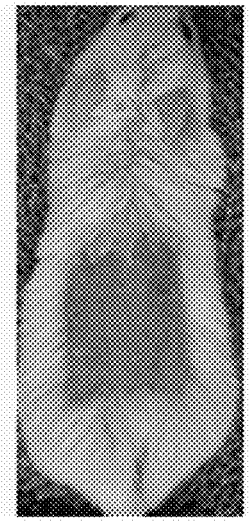
Figure 5:
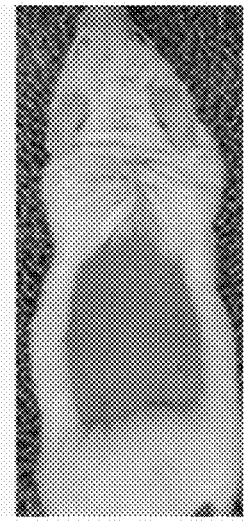

FIG. 5 illustrates the remission of skin lesions with a methyl 4-[9-(6-aminopuryl)]-2(s)-hydroxybutyrate oral formulation in mice with psoriasis. It is a typical representative diagram, showing skin lesions of the normal control group, model control group and treatment group with the methyl 4-[9-(6-aminopuryl)]-2(s)-hydroxybutyrate ointment in mice with psoriasis induced by imiquimod on Day 7.

Figure 6:
Figure 6:
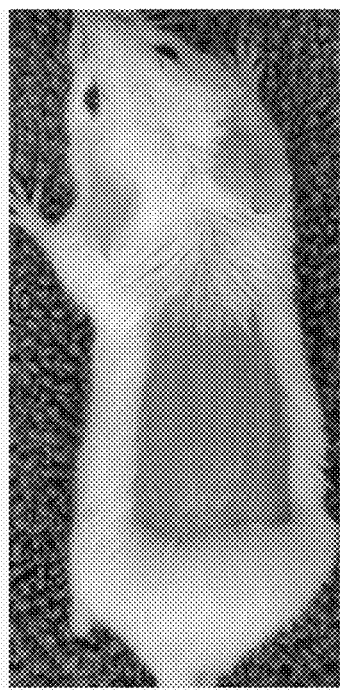

FIG. 6 illustrates the remission of skin lesions with a methyl 4-[9-(6-aminopuryl)]-2(s)-hydroxybutyrate gelatin formulation in mice with psoriasis. It is a typical representative diagram, showing skin lesions of the model control group and treatment group with the methyl 4-[9-(6-aminopuryl)]-2(s)-hydroxybutyrate gelatin formulation in mice with psoriasis induced by imiquimod on Day 6.

Figure 7:
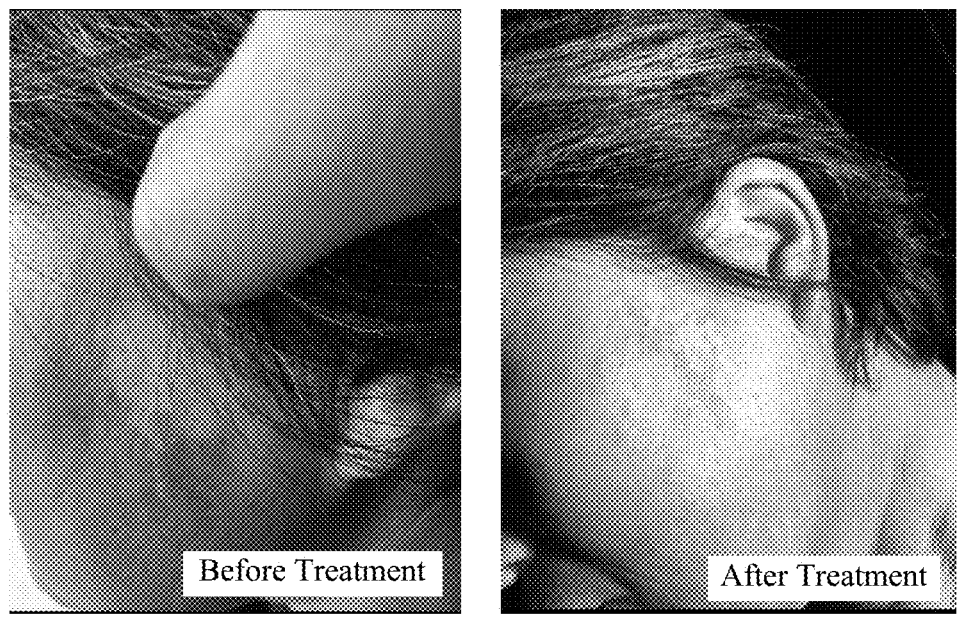

FIG. 7 illustrates the remission of skin lesions with a methyl 4-[9-(6-aminopuryl)]-2(s)-hydroxybutyrate ointment in a vitiligo case.

DETAILED DESCRIPTION OF THE EMBODIMENTS

The invention will be further illustrated by following examples of the invention. The examples are for purposes of illustration or explanation only, and are not to limit the scope claimed by the invention.

Example 1. Preparation of a Methyl 4-[9-(6-aminopuryl)]-2(s)-hydroxybutyrate Ointment Base 1) 15 parts of liquid paraffin, 50 parts of petrolatum, 50 parts of glyceryl monostearate and 100 parts of monostearate were mixed and heated to 70° C. to get an oil phase A;

2) 100 parts of glycerin, 2 parts of triethanolamine, 2 parts of sodium lauryl sulfate and 1 part of ethylparaben were dissolved in 450 parts of purified water and heated to 70° C. to get an aqueous phase B;

3) The oil phase A was slowly added to the aqueous phase B with continuously stirring to fabricate an ointment base, and the ointment base was left to stand and cooled.

Example 2. Preparation of a Methyl 4-[9-(6-aminopuryl)]-2(s)-hydroxybutyrate Ointment 1) 15 parts of liquid paraffin, 50 parts of petrolatum, 50 parts of glyceryl monostearate and 100 parts of monostearate were mixed and heated to 70° C. to get an oil phase A;

2) 100 parts of glycerin, 2 parts of triethanolamine, 2 parts of sodium lauryl sulfate and 1 part of ethylparaben were dissolved in 450 parts of purified water and heated to 70° C., then 15 parts of methyl 4-[9-(6-aminopuryl)]-2(s)-hydroxybutyrate was added to get an aqueous phase B; the aqueous phase B was rapidly stirred to dissolve; the oil phase A was added slowly to the aqueous phase B with continuously stirring to fabricate a methyl 4-[9-(6-aminopuryl)]-2(s)-hydroxybutyrate ointment, and the ointment was left to stand and cooled.

Specifications of the ointment may be selected in accordance with actual needs, 20 g, 30 g, 40 g and other unit dosages are usually employed. Concentration of the methyl 4-[9-(6-aminopuryl)]-2(s)-hydroxybutyrate ointment was 0.125%-8%.

Example 3. Therapeutic Effect of a Methyl 4-[9-(6-aminopuryl)]-2(s)-hydroxybutyrate Ointment on Animal Models with Psoriasis Testing materials: the ointment base from Example 1; the methyl 4-[9-(6-aminopuryl)]-2(s)-hydroxybutyrate ointment from Example 2, and per 10 g of the ointment contains 0.2 g of methyl 4-[9-(6-aminopuryl)]-2(s)-hydroxybutyrate.

Modeling drug: Imiquimod Cream produced by SICHUAN MED-SHINE PHARMACEUTICAL CO., LTD.; SDA (State Drugs Administration) License No.: GUOYAOZHUNZI H20030128; Lot No.: 15060139.

Positive control drug: Calcipotriol Ointment produced by CHONGQING HUAPONT PHARM CO., LTD., SDA (State Drugs Administration) License No.: GUOYAOZHUNZI H20113541; Lot No.: 2015002.

Experimental animals: female balb/c mice with body weight of 18-22 g, provided by SHANGHAI SLAC LABORATORY ANIMAL CO., LTD.

Experimental Method:

Construction of animal models with psoriasis: normal control group, model control group, calcipotriol ointment control group, ointment treatment group, n=10/group. After dorsal hair of the mice were removed, dorsal skin of the mice of the model control group, positive drug control group and ointment treatment group was applied with 62.5 mg of Imiquimod Cream every day. The application was at 7:30 every day and continued for 7 or 15 days.

Figure 1:
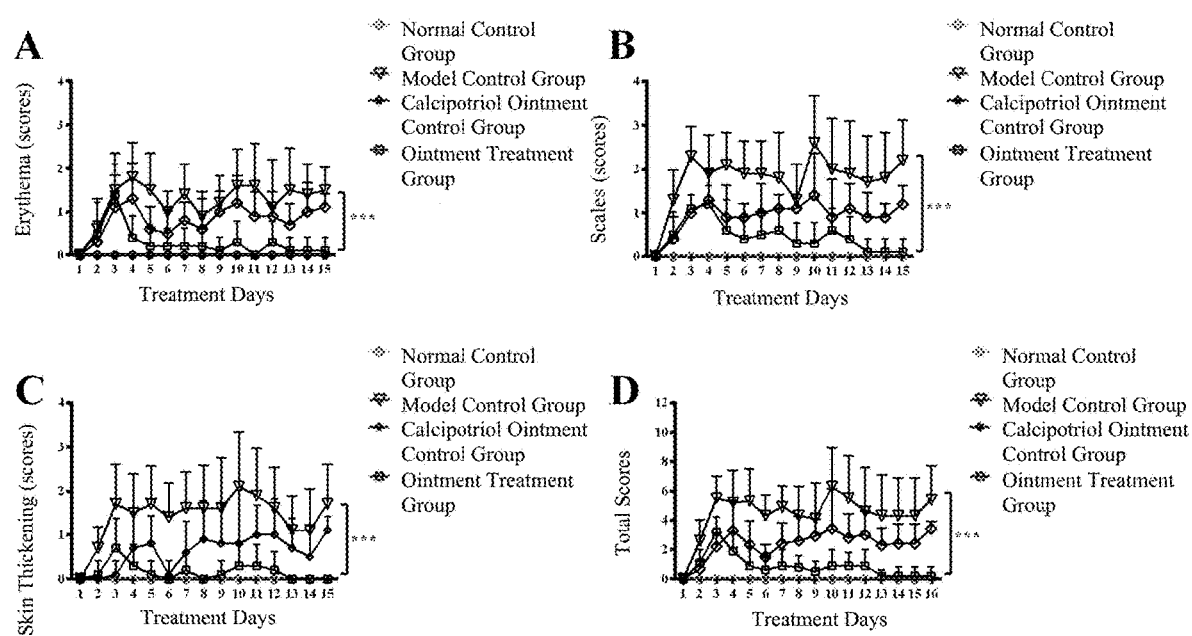
FIG. 1 illustrates the remission of skin lesions with methyl 4-[9-(6-aminopuryl)]-2(s)-hydroxybutyrate in mice with psoriasis. Methyl 4-[9-(6-aminopuryl)]-2(s)-hydroxybutyrate is applied to externally treat psoriasis induced by imiquimod in BALB/c mice every day, and the mice are scored based on psoriasis area and severity index (PASI). The groups in FIG. 1 are the normal control group, model control group, calcipotriol cream control group, and ointment treatment group, n=10/group. ***P<0.001, n=10.

Treatment: dorsal skin of the mice of the normal control group and model control group was applied with ointment base of 62.5 mg from Example 1 every day, and the dorsal skin of the mice of calcipotriol control group was applied with Calcipotriol Ointment of 62.5 mg every day, and the dorsal skin of the mice of ointment treatment group was applied with methyl 4-[9-(6-aminopuryl)]-2(s)-hydroxybutyrate ointment of 62.5 mg. The application was at 18:30 every day and continued for 7 or 15 days. Skin lesion changes of the mice of each group were observed every day in 15 days. Based on PASI score system, the erythema (FIG. 1A), scales (FIG. 1B) and skin thickening (FIG. 1C) of the dorsal skin were scored (0-4). The sum of the three index scores was the total scores of the skin lesion severity (FIG. 1D). The results showed that methyl 4-[9-(6-aminopuryl)]-2(s)-hydroxybutyrate relieved psoriasis induced by imiquimod in mice effectively.

Figure 2:
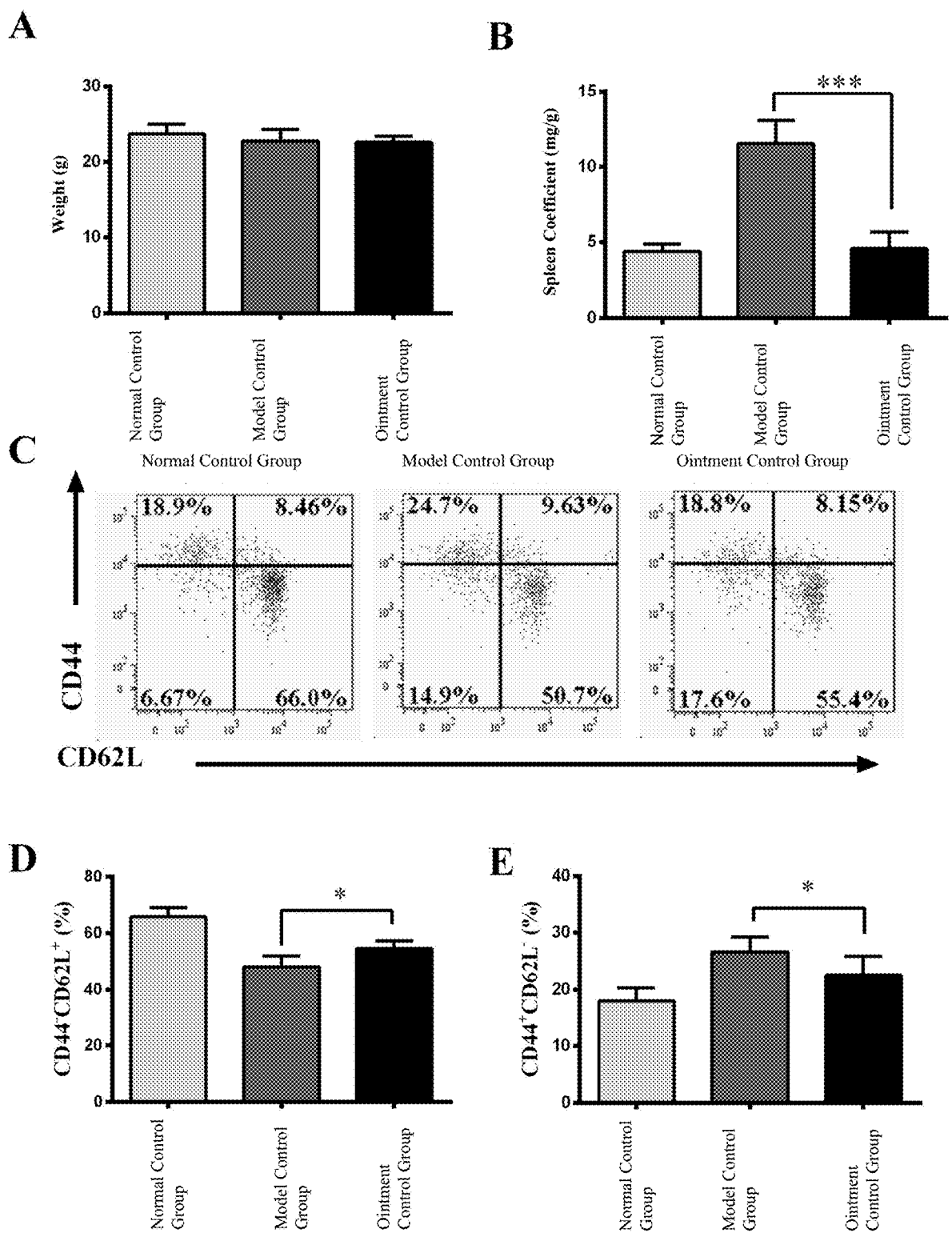
FIG. 2 illustrates the inhibition of spleen swelling and T lymphocyte activation in spleen induced by imiquimod with methyl 4-[9-(6-aminopuryl)]-2(s)-hydroxybutyrate in mice. Mice models are weighed (FIG. 2A) and euthanized on Day 7 of imiquimod-induced psoriasis modeling, and spleens of the mice were weighed to calculate spleen index (FIG. 2B); naive T cells (CD3$^+$CD4$^+$CD44$^-$CD62L$^+$) ratio (FIG. 2C, 2D), and active T cells (CD3$^+$CD4$^+$CD44$^+$CD62L$^-$) ratio (FIG. 2C, 2E) are detected. *P<0.05, ***P<0.001, n≥5. The groups in FIG. 2 are the normal control group, model control group and ointment treatment group.

The mice were weighed when the psoriasis was more serious after 7 days of treatment; the mice were sacrificed, and the spleens of each group were removed and weighed. As shown in FIGS. 2A and 2B, the results showed that the treatment with methyl 4-[9-(6-aminopuryl)]-2(s)-hydroxybutyrate improved spleen swelling in mice with psoriasis induced by imiquimod significantly. Ratio of naive T cells ($CD3^+CD4^+CD44^-CD62L^+$) and their ratio in the spleen lymphocytes were measured by flow cytometry (FIG. 2C, 2D); and ratio of active T cells ($CD3^+CD4^+CD44^+CD62L^-$) and their ratio in the spleen lymphocytes were measured as well (FIG. 2C, 2E). The results showed that methyl 4-[9-(6-aminopuryl)]-2(s)-hydroxybutyrate inhibited T lymphocyte activation in mice with psoriasis induced by imiquimod. Damaged skin of each group was weighed, and mixed with T-PER Tissue Protein Extraction Reagent, by a ratio of 1:20 (w/v, g:mL). Each mixed sample was homogenized and then the precipitate was removed through centrifugation. Inflammatory factor (IL-17) of the extract was detected by ELISA (FIG. 3). The results showed that methyl 4-[9-(6-aminopuryl)]-2(s)-hydroxybutyrate inhibited the level of IL-17 in the damaged skin.

The mice of each group were photographed on Day 7 of treatment, and therapeutic effect of the methyl 4-[9-(6-aminopuryl)]-2(s)-hydroxybutyrate ointment on animal models with psoriasis was observed.

The results showed that the methyl 4-[9-(6-aminopuryl)]-2(s)-hydroxybutyrate ointment relieved psoriasis induced by imiquimod in mice effectively (FIG. 4).

Example 4. Therapeutic Effect of a Methyl 4-[9-(6-aminopuryl)]-2(S)-hydroxybutyrate Oral Formulation on Animal Models with Psoriasis Testing materials: per 5 mg methyl 4-[9-(6-aminopuryl)]-2(s)-hydroxybutyrate was dissolved in 1 mL purified water to get a methyl 4-[9-(6-aminopuryl)]-2(s)-hydroxybutyrate oral formulation with a concentration of 5 mg/mL (w/v).

Modeling drug: Imiquimod Cream produced by SICHUAN MED-SHINE PHARMACEUTICAL CO., LTD; SDA (State Drugs Administration) License No.: GUOYAOZ-HUNZI H20030128; Lot No.: 15060139.

Experimental animals: female balb/c mice with body weight of 18-22 g, were provided by SHANGHAI SLAC LABORATORY ANIMAL CO., LTD.

Experimental Method:
Construction of animal models with psoriasis: normal control group, model control group, oral treatment group, n=10/group. After dorsal hair of the mice were removed, dorsal skin of the model control group, positive drug control group and Calcipotriol Ointment treatment group was applied with 62.5 mg of Imiquimod Cream every day. The application was at 7:30 every day and continued for 7 days.

Treatment: mice of normal control group and model control group were given 0.2 mL water orally every day, and mice of treatment group were orally administrated 0.2 mL the methyl 4-[9-(6-aminopuryl)]-2(s)-hydroxybutyrate oral formulation with concentration of 5 mg/mL every day. It was continued for 7 days. The mice of each group were photographed on Day 7 of the treatment, and therapeutic effect of the methyl 4-[9-(6-aminopuryl)]-2(s)-hydroxybutyrate oral formulation on animal models with psoriasis was observed.

The results showed that the methyl 4-[9-(6-aminopuryl)]-2(s)-hydroxybutyrate oral formulation relieved psoriasis induced by imiquimod in mice effectively (FIG. 5).

Example 5. Therapeutic Effect of a Methyl 4-[9-(6-aminopuryl)]-2(s)-hydroxybutyrate Gelatin Formulation on Animal Models with Psoriasis Testing Materials:
Preparation of a methyl 4-[9-(6-aminopuryl)]-2(s)-hydroxybutyrate gelatin formulation with concentration of 2%: 2 parts of methyl 4-[9-(6-aminopuryl)]-2(s)-hydroxybutyrate were dissolved in 96 parts of purified water to get solution A; 3 parts of sodium carboxymethyl cellulose and 1 part of glycerin were added into the solution A, and stirred to get the methyl 4-[9-(6-aminopuryl)]-2(s)-hydroxybutyrate gelatin formulation with a concentration of 2%.

Preparation of gelatin base: 3 parts of sodium carboxymethyl cellulose and 1 part of glycerin were added into 96 parts of purified water, and stirred to get the gelatin base.

Modeling drug: Imiquimod Cream produced by SICHUAN MED-SHINE PHARMACEUTICAL CO., LTD; SDA (State Drugs Administration) License No.: GUOYAOZ-HUNZI H20030128; Lot No.: 15060139.

Experimental animals: female balb/c mice with body weight of 18-22 g provided by SHANGHAI SLAC LABORATORY ANIMAL CO., LTD.

Experimental Method:
Construction of animal models with psoriasis: model control group, gelatin treatment group, n=10/group. After dorsal hair of the mice were removed, dorsal skin of the model control group and gelatin treatment group was applied with 62.5 mg of Imiquimod Cream every day. The application was at 7:30 every day and continued for 6 days.

Treatment: dorsal skin of the mice of the model control group was applied with the gelatin base 62.5 mg every day, and dorsal skin of the mice of the treatment group was applied with the methyl 4-[9-(6-aminopuryl)]-2(s)-hydroxybutyrate gelatin formulation 62.5 mg every day. The application was at 18:30 every day and continued for 6 days.

The mice of each group were photographed on Day 6 of the treatment, and therapeutic effect of the methyl 4-[9-(6-aminopuryl)]-2(s)-hydroxybutyrate gelatin formulation on animal models with psoriasis was observed.

The results showed that the methyl 4-[9-(6-aminopuryl)]-2(s)-hydroxybutyrate gelatin formulation relieved psoriasis induced by imiquimod in mice effectively (FIG. 6).

Example 6. Therapeutic Effect of a Methyl 4-[9-(6-aminopuryl)]-2(s)-hydroxybutyrate Ointment on a Patient with Vitiligo Chen, female, 54 years old; the patient had had a disease for 4 years, with lesions on the face, the total area was about 4 cm$^2$, being diagnosed with vitiligo. Affected area was applied with the methyl 4-[9-(6-aminopuryl)]-2(s)-hydroxybutyrate ointment from Example 2 in the morning and evening every day, and the application covered all affected area. The skin of the affected part began to turn pink after 11 days of the treatment, the condition was controlled, and pigmentation occurred gradually on the lesions, as shown in FIG. 7.

What is claimed is:
1. A method for treating psoriasis and/or vitiligo, comprising administering an effective amount of medicament comprising methyl 4-[9-(6-aminopuryl)]-2(s)-hydroxybutyrate to a subject in need thereof.
2. The method according to claim 1, wherein a dosage form of the medicament for treating psoriasis and/or vitiligo is an ointment, a gelatin formulation or an oral formulation.

* * * * *